(12) United States Patent
Gagliano et al.

(10) Patent No.: US 7,278,851 B1
(45) Date of Patent: Oct. 9, 2007

(54) PIN CONSTRUCTION FOR TWO-PIECE MODEL AND SYSTEM

(75) Inventors: James Salvatore Gagliano, Tampa, FL (US); Gavin Atlas Steele, IV, White Heath, IL (US)

(73) Assignee: GBase, Inc., Tampa, FL (US)

( * ) Notice: Subject to any disclaimer, the term of this patent is extended or adjusted under 35 U.S.C. 154(b) by 215 days.

(21) Appl. No.: 10/907,246

(22) Filed: Mar. 25, 2005

Related U.S. Application Data

(63) Continuation-in-part of application No. 10/249,945, filed on May 21, 2003, now Pat. No. 6,932,608.

(51) Int. Cl.
*A61C 11/00* (2006.01)
(52) U.S. Cl. .................. 433/213; 433/74
(58) Field of Classification Search .......... 433/213, 433/74
See application file for complete search history.

(56) References Cited

U.S. PATENT DOCUMENTS 4,721,464 A * 1/1988 Roden et al. .................. 433/74
5,201,657 A * 4/1993 Koukos ....................... 433/213

* cited by examiner

*Primary Examiner*—Cris Rodriguez
*Assistant Examiner*—Candice C Stokes
(74) *Attorney, Agent, or Firm*—Ronald E. Smith; Smith & Hopen, P.A.

(57) ABSTRACT

A model and die system includes a working quadrant having an upper flat surface. Pin-receiving tapered bores are formed in the upper flat surface and a thin metallic foil covers the bores. Cast teeth are supported by the working quadrant and each cast tooth has at least one tapered pin depending from it. Each pin includes a tapered main body that matches the taper of the tapered bore, a reduced diameter section of the same taper that accommodates torn or ruptured foil, an annular ramp section that sharply crimps the foil about the entry of the tapered bore, and a tapered rim that matches the taper of the tapered bore to lock the pin into its fully seated position.

7 Claims, 4 Drawing Sheets

PIN CONSTRUCTION FOR TWO-PIECE MODEL AND SYSTEM

CROSS-REFERENCE TO RELATED DISCLOSURE

This disclosure is a continuation-in-part of an earlier disclosure of the same title by the same inventor, filed May 21, 2003 now U.S. Pat. No. 6,932,608, Ser. No. 10/249,945. That disclosure is hereby incorporated by reference into this disclosure.

BACKGROUND OF THE INVENTION

1. Field of the Invention

This invention relates, generally, to dentistry. More particularly, it relates to a model and die system for making casts of dental impressions for the shaping of crowns and dentures.

2. Description of the Prior Art

In the die and model systems now in use, a plurality of tapered bores are formed in a working quadrant. Each tapered bore slideably receives a tapered pin that depends from a cast tooth. A thin, metallic foil covers each tapered bore. The foil is pierced when a pin is introduced into its associated tapered bore.

The seating of a pin in a pin-receiving tapered bore has been a problem in the industry for quite some time. The foil, after having been pierced, often gets in the way and interferes with a proper seating.

In view of the prior art considered as a whole at the time the present invention was made, however, it was not obvious to those of ordinary skill in the pertinent art how to improve the current, unacceptable methods for seating a tapered pin in a tapered bore.

SUMMARY OF THE INVENTION

The long-standing but heretofore unfulfilled need for improvements in two piece die and model systems is now met by a new, useful, and nonobvious invention.

The novel two piece model and die system includes a base, known in the industry as a working quadrant, of generally straight, parallelepiped construction having a flat upper surface. The system further includes a top member, known in the industry as an opposing quadrant, of generally straight, parallelepiped construction having a flat lower surface. The working quadrant and the opposing quadrant are disposed in vertically spaced apart registration with one another. The working quadrant and the opposing quadrant have a common predetermined longitudinal extent, a common predetermined transverse extent, and a common predetermined height.

The working quadrant is solid beneath part of the flat upper surface. At least one row of tapered bores is formed in the working quadrant.

The working quadrant is hollow beneath that part of the flat upper surface where no bores are formed. Each bore is adapted to receive a tapered pin that depends from a cast tooth and gum segment. Thus, the solid part beneath the flat upper surface has a depth sufficient to receive a pin.

A thin metallic foil overlies the flat upper surface of the working quadrant so that dental stone does not flow from or into bores that are not in use.

Each cast tooth of a plurality of cast teeth supported by the working quadrant has at least one pin depending from it. Moreover, a pair of cast teeth, or perhaps a group of three teeth, may be formed as a unit and each unit has at least one tapered pin depending therefrom. Each pin is snugly received within a preselected tapered bore of the plurality of tapered bores formed in the working quadrant. A pin punctures the foil when a cast tooth is mounted on the working quadrant in a manner disclosed hereinafter.

More particularly, the novel model and die system includes a tapered pin having a tapered main body. The tapered main body has a leading end and a trailing end. The leading end has a smaller diameter than the trailing end.

The tapered pin has a reduced diameter section formed integrally with the trailing end of the tapered main body. The taper of the reduced diameter section is substantially equal to the taper of the tapered main body. The diameter of the reduced diameter section is reduced relative to a diameter of the trailing end of the main body of the tapered pin by an amount substantially equal to a thickness of the thin foil.

The tapered pin has an annular ramp formed integrally with the trailing end of the reduced diameter section. The annular ramp has a taper greater than the taper of the tapered main body and the reduced diameter section.

The tapered pin further includes a rim formed integrally with the trailing end of the annular ramp. The taper of the rim is substantially equal to the taper of the tapered main body and the reduced diameter section.

The primary object of this invention is to provide an improved tapered pin to overcome the unsatisfactory seating problems produced by prior art tapered pins.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
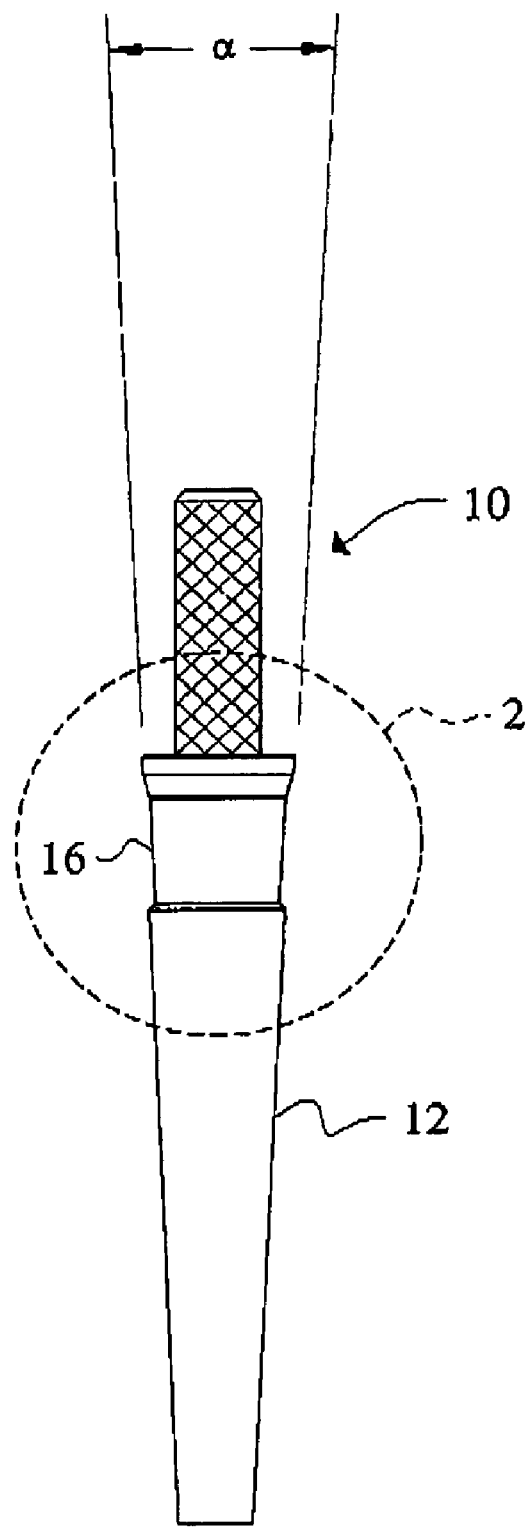
FIG. 1 is a side elevational view of the novel tapered pin, indicating a preferred degree of tapering.

Referring to FIG. 1, it will there be seen that the reference numeral 10 denotes an illustrative embodiment of the novel tapered pin as a whole.

Metal tapered pin 10 has a tapered main body 12 configured and dimensioned to be slidingly received within a tapered bore, not depicted in FIG. 1. The preferred angle of taper a of tapered main body 12 is about five and seventenths degrees (5.7°). Accordingly, the degree of taper measured relative to a longitudinal axis of symmetry of said pin is half that, i.e., two and eighty-five hundredths degrees (2.85°).

Figure 2:
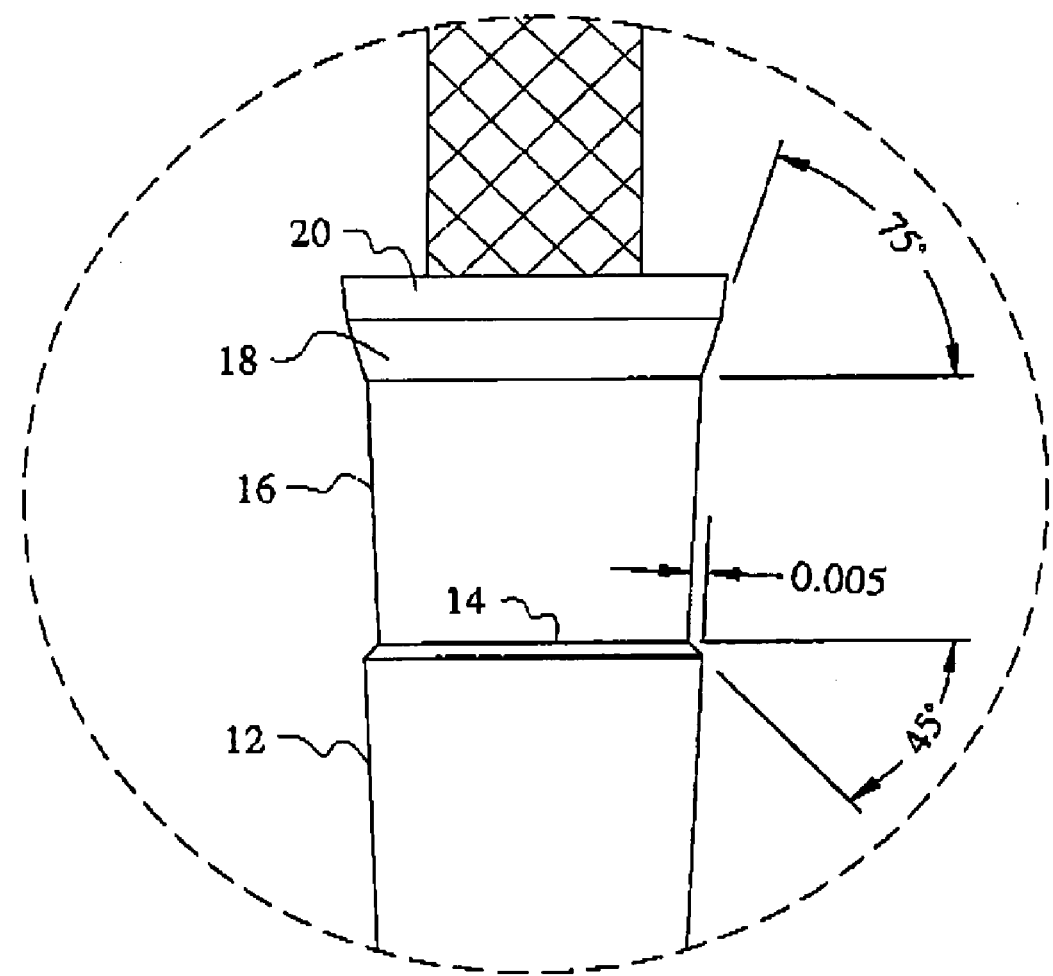
FIG. 2 is an enlarged view of the circled area denoted by the reference numeral 2 in FIG. 1.

As depicted in FIG. 2, the diameter of tapered main body 12 is stepped down at annular step 14, said annular step being formed at the trailing end of said tapered main body 12. The angle of annular step 14 is about forty-five degrees (45°) as indicated in said Fig. The reduction in diameter is about five thousands of an inch (0.005 inch) as also indicated in said Fig. Reduced diameter section 16 is tapered, relative to said longitudinal axis of symmetry, substantially the same as tapered main body 12, i.e., at 2.85° relative to said longitudinal axis of symmetry.

FIG. 2 also discloses that annular ramp 18, formed at the trailing end of reduced diameter section 16, is angled at seventy-five degree (75°) relative to a horizontal axis, i.e., fifteen degrees (15°) relative to said longitudinal axis of symmetry.

Said Fig. also discloses that rim 20 of tapered pin 10, formed at the trailing end of annular ramp 18, is tapered at the same 5.7° taper as main body 12 and reduced diameter section 16, i.e., 2.85° relative to said longitudinal axis of symmetry.

Figure 3:
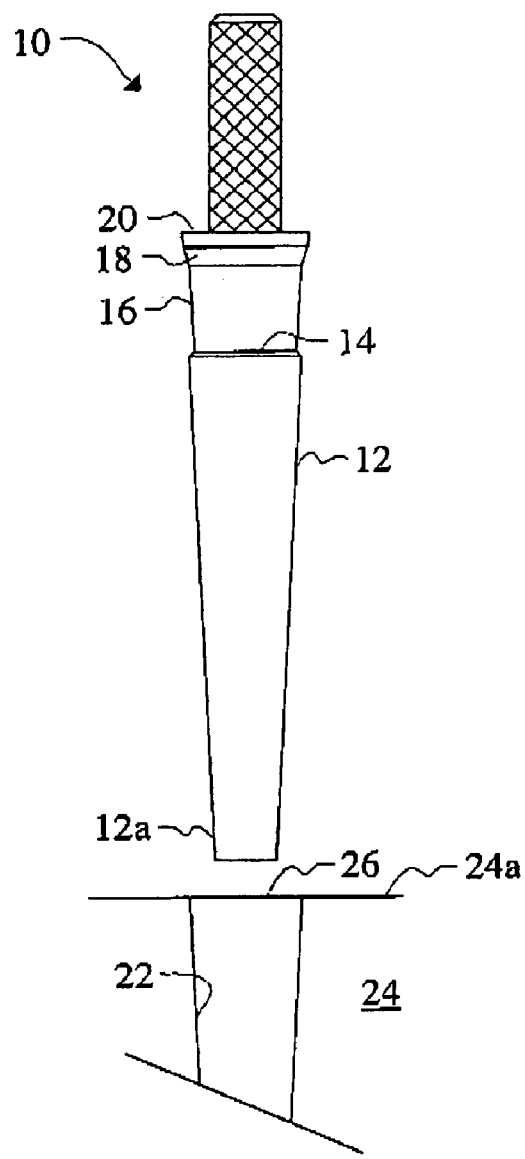
FIG. 3 is a side elevational view of the novel tapered pin positioned above a foil-covered tapered bore.

Referring now to FIG. 3, it will there be seen that tapered bore 22 is formed in working base or quadrant 24 having flat upper surface 24a. The taper of tapered bore 22 is 2.85° relative to the longitudinal axis of pin 10.

A thin, metallic foil 26 overlies and covers said tapered bore 22 to prevent dental stone from falling thereinto.

In FIG. 3, pin 10 is positioned above foil 26, in longitudinal alignment with tapered bore 22, but the foil has not yet been punctured.

Figure 4:
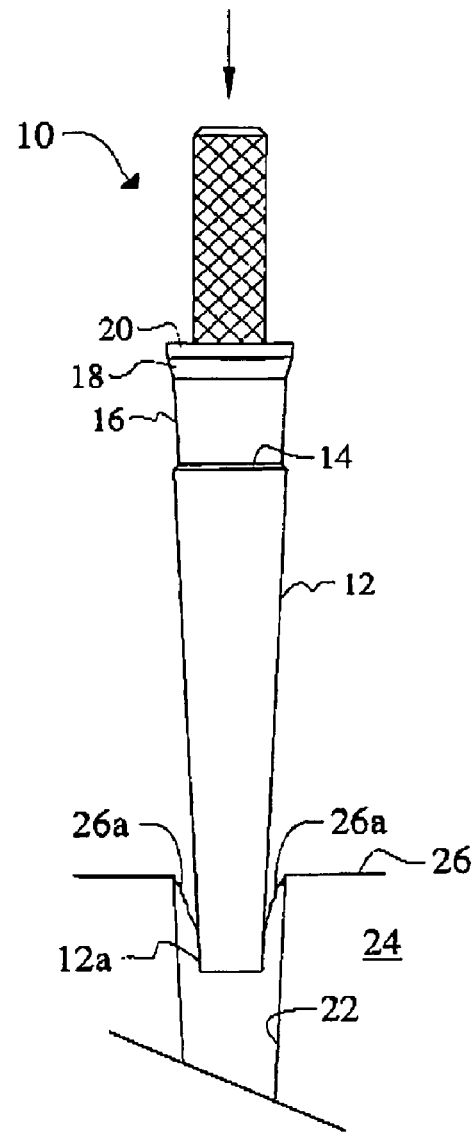
FIG. 4 is a side elevational view of the novel pin after the leading end of the pin has just punctured the foil.

In FIG. 4, leading end 12a of tapered main body 12 has punctured foil 26 and has entered into tapered bore 22. The torn or ruptured foil is denoted 26a. Said ruptured foil 26a is pushed into tapered bore 22 by said leading end 10a.

Figure 5:
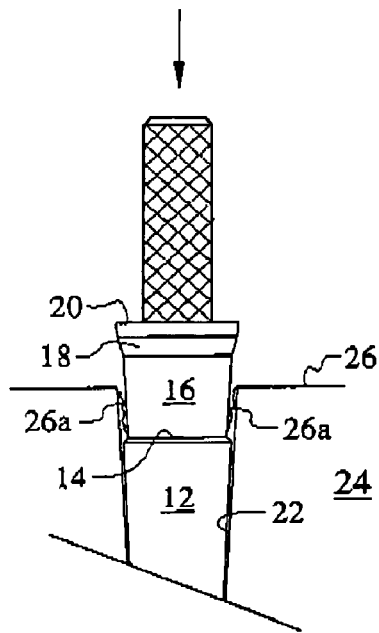
FIG. 5 is a side elevational view of the novel pin when a reduced diameter section of the novel pin has entered into contact with the ruptured foil.

In FIG. 5, reduced diameter section 16 has entered into contact with ruptured foil 26a. Significantly, the thickness of metallic foil 26 is about five thousands of an inch (0.005 inch), i.e., substantially the same as the reduction of diameter at annular step 14. Accordingly, ruptured metallic foil 26a does not interfere with or impede insertion of pin 10 into tapered bore 22.

Figure 6:
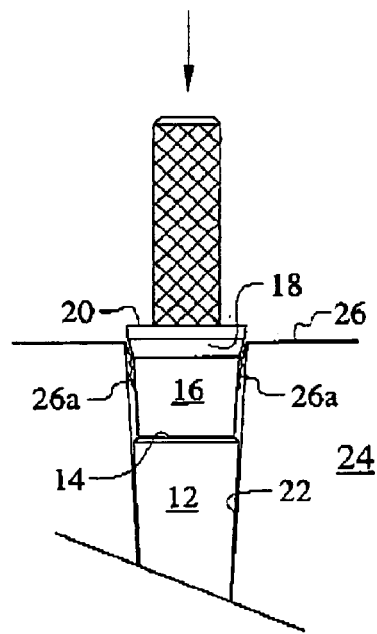
FIG. 6 is a side elevational view of the novel pin when a steeply tapered section thereof has entered into contact with the ruptured foil.

In FIG. 6, pin 10 is inserted still further into tapered bore 22, relative to the FIG. 5 position, and seventy-five degree (75°) annular ramp 18 has engaged foil 26a. Annular ramp 18 firmly presses or crimps foil 26a in a radially outward direction so that the foil that surrounds the opening of tapered bore 22 is pressed very tightly against the peripheral edge of said opening.

The taper of reduced diameter section as aforesaid is 2.85° relative to the longitudinal axis of symmetry of pin 10 and the taper of annular ramp as aforesaid is 15° relative to said longitudinal axis. Thus the angle of taper changes by about 12° (12.15°) where the trailing end of reduced diameter section 16 meets the leading end of annular ramp 18. This abrupt change in the angle of taper puts the crimp into foil 26.

Figure 7:
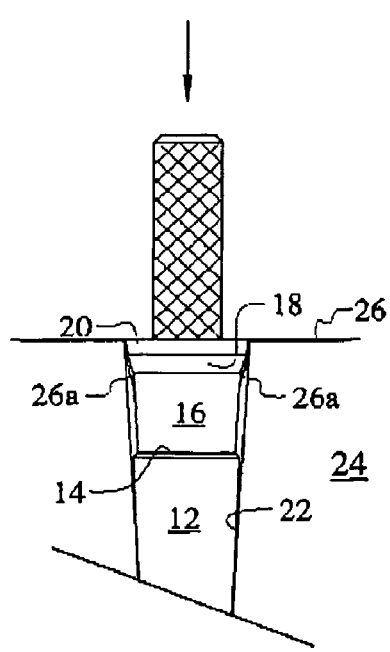
FIG. 7 is a side elevational view of the novel pin after a short tapered section thereof has entered into contact with the ruptured foil.

The final, flush seating of pin 10 is depicted in FIG. 7. Uppermost section or rim 20, formed integrally with the trailing end of annular ramp 18, makes full annular contact with the uppermost end of tapered bore 22 because said rim 20 is tapered at the same angle (2.85°) as said tapered bore as aforesaid. Accordingly, rim 20 binds with the torn foil and locks pin 10 into the fully seated position of FIG. 7.

Thus it is understood that reduced diameter section 16 accommodates torn or ruptured foil 26a, annular ramp section 18 sharply crimps foil 26 about the entry of tapered bore 22, and tapered rim 20 matches the taper of bore 22, thereby locking pin 10 into its fully seated position.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,

What is claimed is:

1. A model and die system, comprising:
a tapered pin;
said tapered pin having a tapered main body;
said tapered main body having a leading end and a trailing end, said leading end having a smaller diameter than said trailing end;
said tapered pin having a reduced diameter section, formed integrally with said trailing end of said tapered main body, said reduced diameter section having a taper substantially equal to and in the same direction as the taper of said tapered main body;
said tapered pin having an annular ramp, formed integrally with a trailing end of said reduced diameter section, said annular ramp having a taper greater than the taper of said tapered main body and said reduced diameter section and said annular ramp taper being in the same direction as said taper of said tapered main body and said reduced diameter section; and
said tapered pin having a rim, formed integrally with a trailing end of said annular ramp, said rim having a taper substantially equal to the taper of said tapered main body and said reduced diameter section and said taper of said rim being in the same direction as the taper of said tapered main body, said reduced diameter section, and said annular ramp.

2. The system of claim 1, further comprising:
a working base having a flat upper surface;
at least one tapered bore formed in said flat upper surface;
at least one cast tooth having at least one tapered pin depending therefrom;
said at least one tapered pin adapted to be fully seated within said tapered bore.

3. The system of claim 2, further comprising:
a thin foil disposed in overlying relation to said flat upper surface to cover said at least one bore, said foil being punctureable by said leading end of said tapered pin.

4. The system of claim 3, further comprising:
said reduced diameter section of said tapered pin having a diameter that is reduced relative to a diameter of said trailing end of said tapered pin by an amount substantially equal to a thickness of said thin foil.

5. The system of claim 4, wherein said thin foil has a thickness of about 0.005 inch and wherein the diameter of said reduced diameter section is about 0.005 inch less than the diameter of said trailing end of said main body of said tapered pin.

6. The system of claim 4, further comprising:
said tapered main body, said reduced diameter section, and said rim having a common taper of about 2.85° relative to a longitudinal axis of symmetry of said pin.

7. The system of claim 4, further comprising:
said annular ramp having a taper of about 15° relative to said longitudinal axis of symmetry of said pin.

* * * * *